(12) United States Patent
Ito et al.

(10) Patent No.: US 10,391,187 B2
(45) Date of Patent: Aug. 27, 2019

(54) APPARATUS FOR VIRUS INACTIVATION AND SAMPLING

(71) Applicant: Toyo Engineering Corporation, Chiyoda-ku, Tokyo (JP)

(72) Inventors: Hiroshi Ito, Narashino (JP); Takaya Nakagawa, Narashino (JP); Yoichi Kitsuta, Narashino (JP)

(73) Assignee: TEC PROJECT SERVICES CORPORATION, Narashino-Shi, Chiba (JP)

( * ) Notice: Subject to any disclaimer, the term of this patent is extended or adjusted under 35 U.S.C. 154(b) by 71 days.

(21) Appl. No.: 15/513,778

(22) PCT Filed: Sep. 15, 2015

(86) PCT No.: PCT/JP2015/076076
§ 371 (c)(1),
(2) Date: Mar. 23, 2017

(87) PCT Pub. No.: WO2016/059925
PCT Pub. Date: Apr. 21, 2016

(65) Prior Publication Data
US 2018/0228927 A1 Aug. 16, 2018

(30) Foreign Application Priority Data
Oct. 14, 2014 (JP) .................................. 2014-210087

(51) Int. Cl.
*A61L 2/00* (2006.01)
*A61L 2/08* (2006.01)
(Continued)

(52) U.S. Cl.
CPC ............ *A61L 2/0088* (2013.01); *A61K 35/76* (2013.01); *A61L 2/24* (2013.01); *A61L 2/28* (2013.01);
(Continued)

(58) Field of Classification Search
CPC ........ A61L 2/24; A61L 2/0023; A61L 2/0035; A61L 2/007; A61K 9/4833
(Continued)

(56) References Cited

U.S. PATENT DOCUMENTS 4,658,655 A  4/1987  Kanno

FOREIGN PATENT DOCUMENTS

JP  2001-070827 A  3/2001
JP  2003-002896 A  1/2003
(Continued)

OTHER PUBLICATIONS

International Search Report for PCT/JP2015/076076 (2 pgs.).
(Continued)

*Primary Examiner* — Monzer R Chorbaji
(74) *Attorney, Agent, or Firm* — Flynn Thiel, P.C.

(57) ABSTRACT

A virus inactivation and sampling apparatus for use in a process of purifying a liquid drug substance. A closed circulation line is formed by an outlet port 11 of a bag 10 containing a liquid drug substance, a first line 41, sampling means 20, a second line 42 (pH meter 30) and an inlet port 12 of the bag 10, and an acidic aqueous solution is fed through an acidic aqueous solution line 45 and circulated to inactivate viruses in the liquid drug substance.

5 Claims, 3 Drawing Sheets

(51) Int. Cl.
  *C07D 235/12* (2006.01)
  *A61K 35/76* (2015.01)
  *A61L 2/24* (2006.01)
  *A61L 2/28* (2006.01)
  *C12N 7/00* (2006.01)
  *A61K 38/00* (2006.01)

(52) U.S. Cl.
  CPC ............... *C12N 7/00* (2013.01); *A61K 38/00* (2013.01); *A61L 2202/123* (2013.01); *A61L 2202/15* (2013.01); *A61L 2202/21* (2013.01)

(58) Field of Classification Search
  USPC ........ 422/1, 22, 27, 28, 292, 307; 548/310.1
  See application file for complete search history.

(56) References Cited

FOREIGN PATENT DOCUMENTS

| | | |
|---|---|---|
| JP | 2009-263231 A | 11/2009 |
| JP | 2011-006489 A | 1/2011 |
| WO | WO 2005/089326 A2 | 9/2005 |
| WO | WO 2006/055632 A2 * | 5/2006 |
| WO | WO 2014/004103 A1 | 1/2014 |

OTHER PUBLICATIONS

English translation of International Preliminary Report on Patentability for PCT/JP2015/076076, dated Apr. 18, 2017, and Written Opinion of the International Searching Authority, dated Dec. 22, 2015 (6 pages).

Kazuya Nakagawa et al., "Introduction to Element Technology in Bio-Pharmaceutical Factory Planning", Piping Technology September Special Issue—Engineering Guidebook for Piping Engineers 2014, published on Sep. 15, 2014, vol. 56, No. 11, pp. 11-21 (6 pages).

Japanese Office Action (Decision of Grant) for corresponding application No. JP 2014-210087, dated Mar. 26, 2019 (3 pages).

\* cited by examiner

[Figure 1]
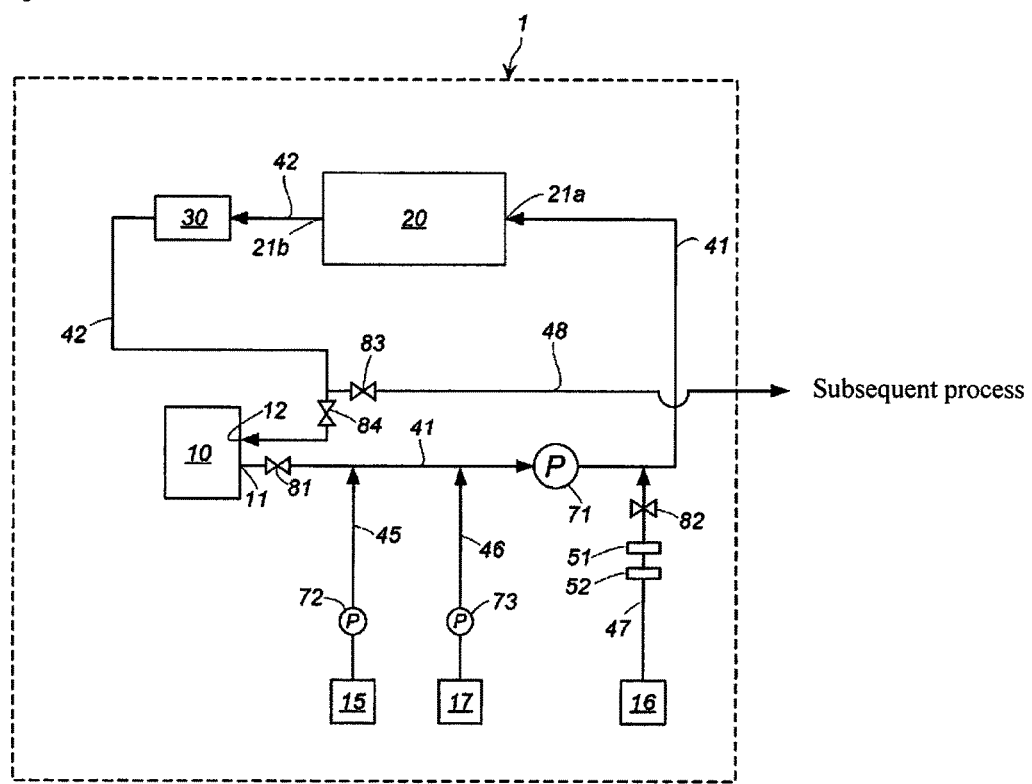
Subsequent process

[Fig. 2]
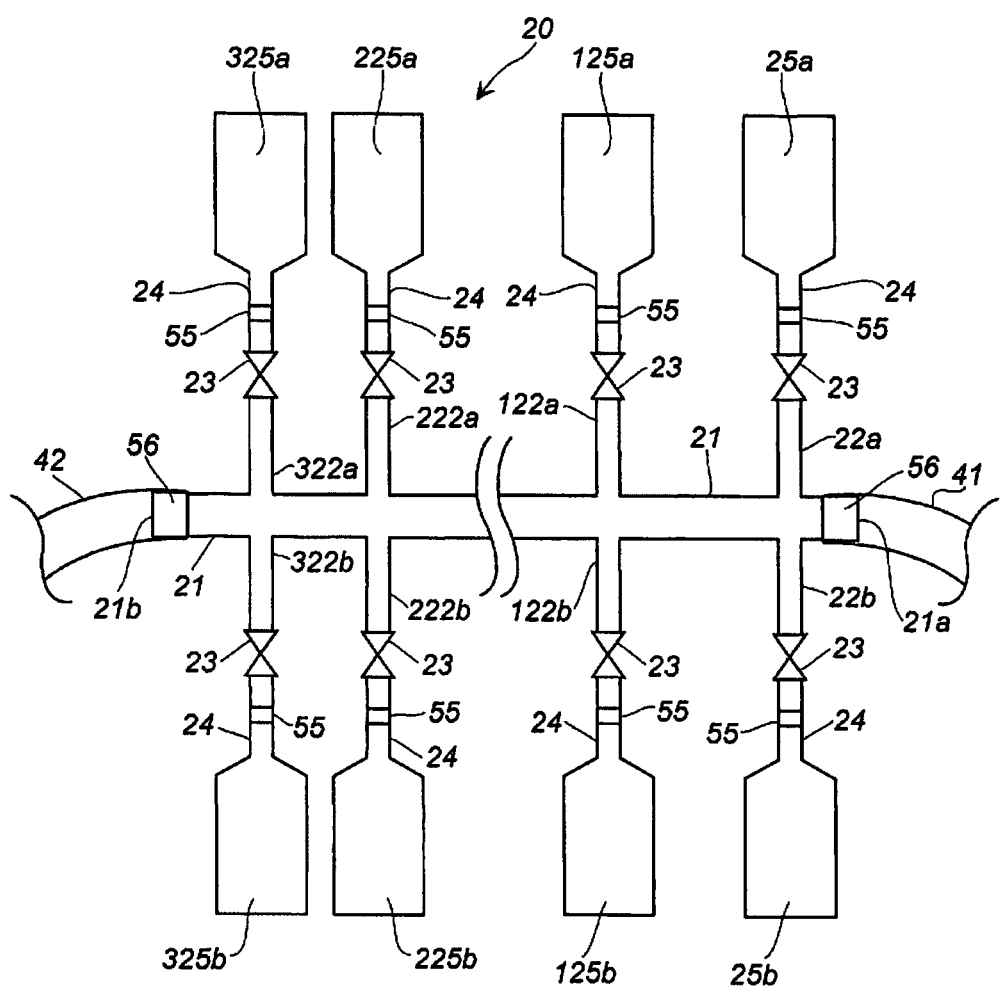

[Fig. 3]
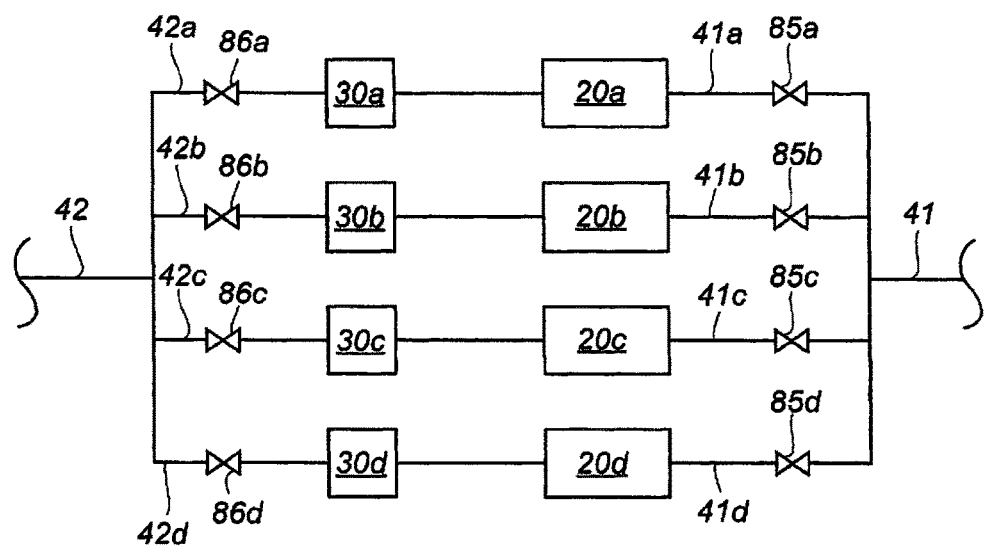

APPARATUS FOR VIRUS INACTIVATION AND SAMPLING

TECHNICAL FIELD

The present invention relates to an apparatus for virus inactivation and sampling used in a process for purifying a drug substance for biopharmaceuticals such as a therapeutic protein.

BACKGROUND ART

As a method for purifying a therapeutic protein, which is well-known as a biopharmaceutical, JP-A 2001-70827 (paragraph number 0002) discloses a method using centrifugation, filtration by a filter, gel chromatography or the like; and JP-A 2011-6489 (claims) discloses a method using affinity chromatography.

Then, a purifying process may include virus inactivation, with which a therapeutic protein is adulterated.

As a method for virus inactivation, JP-A 2003-2896 and JP-A 2009-263231 disclose a method for the contact-processing of a therapeutic protein in a low-pH aqueous solution (paragraph number 0032 of JP-A 2003-2896; and claims of JP-A 2009-263231).

When virus inactivation treatment is conducted on a therapeutic protein, sampling is necessary in order to check that viruses in the therapeutic protein are inactivated. Further, JP-A 2009-263231 indicates in Examples (Tables 1 to 6) the relationship between pH and the virus inactivating efficiency.

In order to prevent therapeutic proteins from being contaminated, it is desired to automate such inactivation and sampling in a closed system.

SUMMARY OF INVENTION

The present invention has an object of providing an apparatus for virus inactivation and sampling used in a process for purifying a liquid drug substance, wherein the apparatus can automatically conduct an inactivation treatment in a closed system, and then further, sampling.

The present invention provides an apparatus for virus inactivation and sampling for use in a process of purifying a liquid drug substance, and a method for operating the apparatus, the apparatus including a bag having an outlet port and an inlet port and containing the liquid drug substance, means for inactivating a virus in the liquid drug substance in the bag, and sampling means for checking inactivation of the virus, wherein:

the virus inactivation means can feed an acidic aqueous solution to the liquid drug substance and can measure the pH of the liquid drug substance;

the sampling means has a main tube and a plurality of branch tubes branched from the main tube and the branch tubes are connected with heat fusible tubes extending from openings of a plurality of sampling containers;

the outlet port of the bag containing the liquid drug substance and a first end of the main tube of the sampling means are connected to each other by a first line via a liquid delivery pump for the liquid drug substance;

a second end of the main tube of the sampling means and the inlet port of the bag containing the liquid drug substance are connected to each other by a second line;

the first line is connected with a liquid delivery line for the acidic aqueous solution and the second line is connected with a pH meter; and the outlet port of the bag containing the liquid drug substance, the first line, the sampling means, the second line and the inlet port of the bag containing the liquid drug substance forma closed circulation line.

In a preferable embodiment, an air line, a liquid delivery line for a neutralizer aqueous solution and a liquid delivery pump for the liquid drug substance are further connected to the first line.

In another preferable embodiment, the bag containing the liquid drug substance is placed on a temperature control plate for controlling the temperature of the drug substance.

In further another preferable embodiment, a subsequent process liquid delivery line for delivering the liquid drug substance to a subsequent process is connected between the pH meter of the second line and the inlet port of the bag containing the liquid drug substance.

Also, in a method for operating an apparatus for virus inactivation and sampling of the present invention, the inactivation of a virus in the liquid drug substance is performed by:

circulating the liquid drug substance from the bag containing the liquid drug substance through the circulation line; feeding the acidic aqueous solution from an acidic aqueous solution tank to the first line; measuring with the pH meter a pH of the liquid drug substance in the circulation line; and completing the virus inactivation when the liquid drug substance reaches a predetermined pH value and the pH value is maintained for a predetermined time period, and the sampling of the liquid drug substance is performed by:

conducting sampling at least two times, before the start of delivery of the acidic aqueous solution and at the time when virus inactivation is completed; and sampling from the main tube of the sampling means through the branch tube and the heat fusible tube into the sampling container, thereafter fusing a portion of the heat fusible tube by heat thereby to seal an outlet port of the sampling container, and cutting off the heat fusible tube between the branch tube and the heat fused portion.

The apparatus of the present invention has a bag containing a liquid drug substance, means for conducting an inactivation treatment on viruses in the bag, and sampling means for checking inactivation of the viruses, and these are connected by a closed circulation line, so that contamination from an external atmosphere is prevented.

Since the circulation line is automatically operated, no manual work is directly involved when virus inactivation treatment and sampling are conducted, thus preventing a wrong operation and achieving labor savings.

The apparatus for virus inactivation and sampling of the present invention is used in a process of purifying a liquid drug substance, and enables automatic operation of: inactivation of viruses in the liquid drug substance; and sampling of the liquid drug substance before and after the inactivation treatment, thereby stabilizing the quality of a product at a high level.

BRIEF DESCRIPTION OF DRAWINGS

The present invention will be further fully understood by the following detailed description and accompanying drawings, but these are attached hereto only for explanation and they are not for limiting the present invention.

FIG. 1 is a schematic view showing the apparatus for virus inactivation and sampling according to the present invention.

FIG. 2 is a plan view showing one embodiment of sampling means.

FIG. 3 is a schematic view showing another embodiment of sampling means.

DETAILED DESCRIPTION OF THE INVENTION

Apparatus for Virus Inactivation and Sampling

A process of purifying a liquid drug substance is, for example, a process of purifying a therapeutic protein, which includes, if there is a possibility of virus contamination, virus inactivation by combining affinity chromatography and a plurality of other chromatographies.

An apparatus 1 (which corresponds to a portion enclosed by a dotted line in FIG. 1) of the present invention may be used during such purifying process; and it may be used, for example, after a therapeutic protein is separated by an affinity chromatography, and subsequent thereto, before purifying treatments by a plurality of chromatographies, but the usage is not limited thereto.

The apparatus 1 of the present invention has a bag 10 containing a liquid drug substance, means for inactivating viruses, which are possibly present in the liquid drug substance in the bag 10, and sampling means 20 for checking the inactivation of the viruses.

The means for conducting an inactivation treatment on viruses in the liquid drug substance is composed of adding means (first inactivating means) for adding to the liquid drug substance an acidic aqueous solution for virus inactivation, and pH measuring means (second inactivating means) for checking the pH of the liquid drug substance, to which the acidic aqueous solution has been added.

In the bag 10, the liquid drug substance (for example, therapeutic protein) is contained.

The material or the shape of the bag 10 is not particularly limited, but the bag is preferably formed of a thermoplastic resin or rubber and preferably has such a transparency that an interior thereof can be visually observed.

The volume of the bag 10 may be selected depending on the amount of produced liquid drug substance, but it is preferably 5 to 30 L in terms of completing inactivation in a short time period.

The bag 10 has an outlet port 11 and an inlet port 12.

The outlet port 11 is a tube having: a first end side, which is inserted into the bag 10; and a second end side opposite thereto, which is extended to outside of the bag 10, and the tube is integrated with a first line 41.

The inlet port 12 is a tube having: a first end side, which is inserted into the bag 10; and a second end side opposite thereto, which is extended to outside of the bag 10, and the tube is integrated with a second line 42.

The outlet port 11 and the inlet port 12 are formed at an interval on the same surface of the bag 10 in FIG. 1, but they may be formed on a different surface and may be formed, for example, on opposite surfaces to each other.

The bag 10 is placed on a temperature control plate, and thereby, enabling the temperature of the liquid drug substance in the bag to be controlled. When the temperature is controlled, it is preferably about 20° C. to 30° C., for example.

The outlet port 11 of the bag 10 and the sampling means 20 are connected to each other by the first line 41.

On the way of the first line 41, a pinch valve (electromagnetic valve) 81 and a liquid delivery pump 71 are installed.

The sampling means 20 and the inlet port 12 of the bag 10 are connected to each other by the second line 42.

As the sampling means 20, one illustrated in FIG. 2 may be used.

The sampling means 20 has: a main tube 21 having a first end 21a and a second end 21b opposite thereto; and branch tubes 22a, 22b, branch tubes 122a, 122b, branch tubes 222a, 222b and branch tubes 322a, 322b branched from plural locations of the main tube 21 in opposite directions.

The first end 21a of the main tube 21 is connected to the first line 41 via an aseptic connector 56; and the second end 21b is connected to the second line 42 via an aseptic connector 56.

For the main tube 21, the branch tubes 22, 22b and others, a tube formed of a thermoplastic resin or rubber (for example, thermally-infusible silicone rubber) may be used, but one having such transparency that an interior thereof can be visually observed is preferably used.

The plural branch tubes 22a, 122a, 222a and 322a are connected to heat fusible tubes 24 extending from openings of sampling containers 25a, 125a, 225a and 325a via connectors 55. Pinch valves 23 are attached to the plural branch tubes, respectively.

The plural branch tubes 22b, 122b, 222b and 322b are connected to heat fusible tubes 24 extending from openings of sampling containers 25b, 125b, 225b and 325b via connectors 55. The pinch valves 23 are attached to the plural branch tubes, respectively.

As the main tube 21, a tube having an inner diameter of about 9 to 10 mm may be used.

The branch tubes 22a, 22b and others may have a smaller inner diameter than the main tube 21, but in terms of preventing the liquid drug substance from remaining inside due to surface tension, they preferably have an inner diameter of about 6 to 7 mm.

The sampling containers 25a, 25b and others are preferably kept at a low temperature so that the extinction of viruses by heat during sampling does not affect the checking of inactivation and deterioration such as thermal denaturation of a therapeutic protein is prevented.

For the heat fusible tube 24, a tube formed of a publicly-known thermoplastic resin or thermoplastic rubber may be used.

The sampling containers 25a, 25b and others preferably have a bottle shape or bag shape with an opening, and for them, one formed of a thermoplastic resin or glass may be used.

In the sampling containers 25a, 25b and others, the heat fusible tube 24 is preferably integrated with the opening from the viewpoint of preventing a sampled liquid drug substance from being contaminated.

The number of the branch tubes and the sampling containers can be adjusted in response to the number of samplings.

First inactivating means is connected to the first line 41 between the bag 10 and the pump 71.

The first inactivating means is composed of an acidic aqueous solution tank 15, a liquid delivery pump 72 for an acidic aqueous solution, and a liquid delivery line 45 for an acidic aqueous solution.

As the acidic aqueous solution in the acidic aqueous solution tank 15, usable is an aqueous solution of arginine or an arginine derivative having an appropriately-adjusted pH disclosed in, for example, JP-A 2009-263213.

A pH meter 30 as second inactivating means is connected to the second line.

To the first line 41, the liquid delivery line 45 for an acidic aqueous solution, a liquid delivery line 46 for a neutralizer aqueous solution, the pump 71 and an air line 47 are connected in this order from the outlet port 11 of the bag 10.

The pump 71 may be arranged between the outlet port 11 of the bag 10 and the liquid delivery line 45 for an acidic aqueous solution in FIG. 1.

The air line 47 connects an air tank 16 filled with sterile air by pressure to the first line 41, and a sterile filter 51, a pressure reducing valve 52 and a pinch valve 82 are arranged.

The liquid delivery line 46 for a neutralizer aqueous solution connects a neutralizer aqueous solution tank 17 to the first line 41, and a liquid delivery pump 73 for a neutralizer aqueous solution is arranged.

A neutralizer is for neutralizing the liquid drug substance after inactivation by the addition of the acidic aqueous solution, and a pharmaceutically acceptable neutralizer is used.

Between the pH meter 30 of the second line 42 and the inlet port 12 of the bag 10 containing the liquid drug substance, a subsequent process liquid delivery line 48 is connected, which is for delivering the liquid drug substance after the completion of virus inactivation to a subsequent process.

A pinch valve 84 is arranged between: a branch portion in the second line 42 for the subsequent process liquid delivery line 48; and the inlet port 12 of the bag 10.

A pinch valve 83 is arranged in the subsequent process liquid delivery line 48 at a side close to the second line 42.

In the apparatus 1, a combination of a plurality of sampling means and a plurality of pH meters, as shown in FIG. 3, may be used.

In FIG. 3, the first line 41 illustrated in FIG. 1 is branched into four first lines 41a, 41b, 41c and 41d, and each of them is connected to each of four sampling means 20a to 20d, which is the same as illustrated in FIG. 2.

Pinch valves 85a to 85d are arranged to first lines 41a to 41d, respectively.

Further, in FIG. 3, the second line 42 illustrated in FIG. 1 is branched into four second lines 42a, 42b, 42c and 42d, and they are connected to four pH meters 30a to 30d, respectively.

Pinch valves 86a to 86d are arranged to second lines 42a to 42d, respectively.

Further, in the embodiment of FIG. 3, the four sampling means 20a to 20d may share one pH meter.

The material of the lines including the first line 41 and the second line 42 illustrated in FIG. 1 is not particularly limited as long as it can maintain a closed state, and a flexible tube formed of a thermoplastic resin or rubber (preferably silicone rubber) is preferable, and one having such a transparency that an interior thereof can be visually observed is more preferable.

Each of pinch valves shown in FIGS. 1 to 3 is electrically connected to a power source by a lead wire, which is not illustrated.

Further, if necessary, a pinch valve may be appropriately arranged, other than the pinch valves shown in FIGS. 1 to 3.

As shown in FIG. 1, the apparatus 1 has a closed circulation line, which is composed of the outlet port 11 of the bag 10 containing the liquid drug substance, the first line 41, the sampling means 20, the second line 42 (including the pH meter 30) and the inlet port 12 of the bag containing the liquid drug substance.

Constituent elements of the apparatus 1 of the present invention are sterilized before being connected to one another.

Except for the pumps 71 to 73, the pH meter 30, the pinch valves, the sterile filter 51 and the pressure reducing valve 52, the constituent elements of the apparatus 1 of the present invention are disposable at the time when sampling can no longer be conducted.

Method for Operating the Apparatus 1

Both inactivation of a virus in the liquid drug substance in the bag 10 and sampling for checking the inactivation can be carried out by automatically operating the apparatus 1 shown in FIG. 1.

Before the start of the automatic operation of the apparatus 1, a check test (air leak test) on whether the circulation line is in a closed state may be carried out.

In a state where the pinch valves 81, 83 and 84 are closed, the pinch valve 82 is opened, air (sterile air) in the air tank 16 is fed through the air line 47 to the first line 41, and the circulation line is filled with air.

Whether the circulation line is closed or not can be checked by checking whether an air leakage occurs in this state.

The sterile air after the check test is discharged from a gas discharge line provided to the bag 10.

First, a method for virus inactivation is explained.

In a state where the pinch valves 81 and 84 of the first line 41 are opened and the pinch valve 83 of the subsequent process liquid delivery line 48 is closed, the liquid delivery pump 71 is driven to deliver the liquid drug substance from the outlet port 11 of the bag 10.

The liquid drug substance delivered from the first line 41 enters into the main tube 21 of the sampling means 20 shown in FIG. 2. At this time, all of the pinch valves 23 of the branch tubes are closed.

The liquid drug substance having passed through the main tube 21 enters the second line 42, and passes through the pH meter 30. At this time, the pH meter 30 measures the pH of the liquid drug substance.

Thereafter, the liquid drug substance further returns from the second line 42 to the inlet port 12 of the bag 10, and enters into the bag 10.

Then, the liquid drug substance is delivered again from the outlet port 11 of the bag 10 to the first line 41. At this time, the liquid delivery pump 72 for an acidic aqueous solution is driven to feed the acidic aqueous solution in the acidic aqueous solution tank 15 through the liquid delivery line 45 to the first line 41.

Thereafter, the pH of the liquid drug substance is continuously measured while circulation operation is repeated by use of the circulation line.

Then, when the liquid drug substance reaches a predetermined pH value (for example, pH 3 to 5) and the pH is maintained for a predetermined time period (for example, 30 to 60 minutes), this state is taken as completion of virus inactivation.

The above-described predetermined pH and time period are different depending on the kind of liquid drug substance, and the amount or the specification of the liquid drug substance in the bag 10, so the pH and the time period for enabling the inactivation are checked by a preliminary test.

Next, a sampling method is explained.

The number of samplings of the liquid drug substance is not particularly limited, but sampling is conducted at least two times, before the start of liquid delivery of the acidic aqueous solution and when virus inactivation is completed.

At a first sampling, in the sampling means 20 of FIG. 2, only the pinch valve 23 of the branch tube 22a is opened and a predetermined amount (for example, 5 to 15 ml) of the liquid drug substance is collected in the sampling container 25a.

Thereafter, after the pinch valve 23 of the branch tube 22a is closed and the automatic operation is finished, the thermoplastic tube 24 is fused by heat or heat-sealed and cut off between a heat-sealed portion and the pinch valve 23. As this keeps the sampling container 25a in a closed state, contamination from an external atmosphere can be completely prevented.

At a second sampling, the liquid drug substance after the completion of virus inactivation is collected.

At the second sampling, in the sampling means 20 of FIG. 2, only the pinch valve 23 of the branch tube 22b is opened and a predetermined amount (for example, 5 to 15 ml) of the liquid drug substance is collected in the sampling container 25b.

Thereafter, after the pinch valve 23 of the branch tube 22b is closed and the automatic operation is finished, the thermoplastic tube 24 is heat-sealed and cut off between a heat-sealed portion and the pinch valve 23. As this keeps the sampling container 25b in a closed state, contamination from an external atmosphere can be completely prevented.

By using liquid drug substances in the sampling containers 25a, 25b to carry out a virus check test, it is confirmed that viruses contained in the drug substance in the sampling container 25a are inactivated.

After the confirmation of virus inactivation, the liquid delivery pump 73 for a neutralizer aqueous solution is driven while the circulation operation is further continued, and the neutralizer aqueous solution in the neutralizer aqueous solution tank 17 is fed to the first line 41 through the liquid delivery line 46.

Thereafter, the liquid drug substance is neutralized while the circulation operation is repeated by use of the circulation line.

The time at which the pH becomes near 7 (for example, 6.8 to 7.2) is taken as an end of the neutralization.

Thereafter, the pinch valve 84 is closed and the pinch valve 83 is opened, and then the liquid drug substance that has been subjected to virus inactivation treatment is sent through the subsequent process liquid delivery line 48 to a subsequent process (for example, a purifying process by a plurality of chromatographies).

Next, a case of using the sampling means of the embodiment of FIG. 3 is explained.

This embodiment is brought into the same state as for the sampling means 20 and the pH meter 30 shown in FIGS. 1 and 2 by opening the pinch valves 85a, 86a and closing other pinch valves.

In this state, sampling is conducted in the same manner as above. Thereafter, some pinch valves are opened and the other pinch valves are closed in the same manner, and the same sampling is repeated.

Further, in the embodiment of FIG. 3, the pinch valves 85a, 85b and the pinch valves 86a, 86b are opened and the other pinch valves are closed, and then, sampling can be conducted.

The embodiment of FIG. 3 is suitable for a case where the number of samplings is large.

Thereafter, a bag 10 containing a new liquid drug substance is incorporated into the apparatus 1, and virus inactivation and sampling are carried out.

At this time, a tube integrally connected with an outlet port 11 of the bag 10 in advance is connected with the pump 71 and then sterilized, and used as the first line 41 from the bag 10 to the pump 71.

Further, a tube integrally connected with an inlet port 12 of the bag 10 in advance is connected with the pH meter 30 and then sterilized, and used as the second line 42 from the bag 10 to the pH meter 30.

In addition, for example, when one production batch is composed of five bags 10, the above-described disposable constituent elements are discarded when inactivation and sampling of the five bags are finished.

Since it is considered that the liquid drug substance remains inside the main tube and the branch tubes of the sampling means 20, an operation for discharging it may be conducted.

As a method for discharging the remaining liquid drug substance, one or both of first and second discharge methods may be conducted.

The first discharge method is a method wherein reverse operation of the pump 71 sucks and discharges the remaining liquid drug substance.

When the first discharge method is adopted, a discharge line with a pinch valve is formed in the first line 41 between the sampling means 20 and the pump 71.

The second discharge method is flushing cleaning (pressure accumulation cleaning) by the use of: sterile air; or sterile air and sterile water.

When this flushing cleaning is adopted, a discharge line with a pinch valve is formed in advance in the second line 42, for example, from the pH meter 30 to the pinch valve 84.

In a state where the pinch valves 81, 83 and 84 are closed, the pinch valve 82 is opened, air (sterile air) in the air tank 16 is fed to the first line 41 through the air line 47, and the circulation line is filled with the air. When sterile air and sterile water are used in combination, sterile water is fed to the circulation line by use of a pump from a sterile water tank provided separately.

Air (or sterile air and sterilized water) is fed until a predetermined pressure is obtained. Then, in a state where the pinch valve 82 is closed, the pinch valve of the discharge line is opened and the pressure inside the circulation line is reduced at once, thereby discharging the remaining liquid drug substance inside the circulation line with the sterile air or the sterile air and sterile water.

The apparatus for virus inactivation and sampling of the present invention can be used in a process of purifying a liquid drug substance such as a therapeutic protein.

LIST OF REFERENCE NUMERALS

1 Apparatus for virus inactivation and sampling
10 Bag containing a liquid drug substance
20 Sampling means
30 pH meter The present invention has been described as above. It is natural that various modifications are included within the scope of the present invention, and these modifications are not departed from the scope of the present invention. In addition, all that is obviously taken as modifications of the present invention by those skilled in the art is within the scope of claims described below.

The invention claimed is:

1. An apparatus for virus inactivation and sampling in a process of purifying a liquid drug substance, comprising a receptacle having an outlet port and an inlet port and containing the liquid drug substance therein, means for inactivating a virus in the liquid drug substance in the receptacle and sampling means for checking the inactivation of the virus, wherein:

the virus inactivation means is configured to feed an acidic aqueous solution to the liquid drug substance and measure the pH of the liquid drug substance;

the sampling means has a main tube, a plurality of branch tubes branching from the main tube and pinch valves provided in the branch tubes for closing the branch tubes and cutting off a heat fusible tube between a heat-sealed portion and a pinch valve, the branch tubes being connected with heat fusible tubes extending from openings of a plurality of sampling containers;

the outlet port of the receptacle containing the liquid drug substance and a first end of the main tube of the sampling means are connected to each other by a first line via a liquid delivery pump for the liquid drug substance;

a second end of the main tube of the sampling means and the inlet port of the receptacle containing the liquid drug substance are connected to each other by a second line;

the first line is connected with a liquid delivery line for the acidic aqueous solution and the second line is connected with a pH meter; and the outlet port of the receptacle containing the liquid drug substance, the first line, the sampling means, the second line and the inlet port of the receptacle containing the liquid drug substance forming a single closed circulation line.

2. The apparatus for virus inactivation and sampling according to claim 1, wherein an air line, a liquid delivery line for a neutralizer aqueous solution and a liquid delivery pump for the liquid drug substance are further connected to the first line.

3. The apparatus for virus inactivation and sampling according to claim 1, wherein the receptacle containing the liquid drug substance is placed on a temperature control plate for controlling the temperature of the drug substance.

4. The apparatus for virus inactivation and sampling according to claim 1, wherein a subsequent process liquid delivery line for delivering the liquid drug substance to a subsequent process is connected between the pH meter of the second line and the inlet port of the receptacle containing the liquid drug substance.

5. A method for operating an apparatus for virus inactivation and sampling, the apparatus comprising a receptacle having an outlet port and an inlet port and containing the liquid drug substance therein, means for inactivating a virus in the liquid drug substance in the receptacle and sampling means for checking the inactivation of the virus, wherein:

the virus inactivation means is configured to feed an acidic aqueous solution to the liquid drug substance and measure the pH of the liquid drug substance;

the sampling means has a main tube, a plurality of branch tubes branching from the main tube and pinch valves provided in the branch tubes for closing the branch tubes and cutting off a heat fusible tube between a heat-sealed portion and a pinch valve, the branch tubes being connected with heat fusible tubes extending from openings of a plurality of sampling containers;

the outlet port of the receptacle containing the liquid drug substance and a first end of the main tube of the sampling means are connected to each other by a first line via a liquid delivery pump for the liquid drug substance;

a second end of the main tube of the sampling means and the inlet port of the receptacle containing the liquid drug substance are connected to each other by a second line;

the first line is connected with a liquid delivery line for the acidic aqueous solution and the second line is connected with a pH meter;

the outlet port of the receptacle containing the liquid drug substance, the first line, the sampling means, the second line and the inlet port of the receptacle containing the liquid drug substance forming a single closed circulation line, and the deactivation of a virus in the liquid drug substance is performed by:

circulating the liquid drug substance from the receptacle containing the liquid drug substance through the circulation line;

feeding the acidic aqueous solution from an acidic aqueous solution tank to the first line;

measuring the pH of the liquid drug substance in the circulation line with a pH meter; and completing the virus inactivation when the liquid drug substance reaches a predetermined pH value and the pH value is maintained for a predetermined time period, sampling of the liquid drug substance being performed by conducting sampling at least two times before the start of delivery of the acidic aqueous solution and at the time when viral deactivation is completed and sampling the liquid drug substance from the main tube through the branch tube and the heat fusible tube into the sampling container, closing the pinch valve attached to the branch tube, thereafter fusing a portion of the heat fusible tube by heat between the pinch valve and the opening of the sampling container thereby to seal an outlet port of the sampling container; and cutting off the heat fusible tube between the pinch valve and the heat-sealed portion of the heat fusible tube.

* * * * *

UNITED STATES PATENT AND TRADEMARK OFFICE
CERTIFICATE OF CORRECTION

PATENT NO. : 10,391,187 B2
APPLICATION NO. : 15/513778
DATED : August 27, 2019
INVENTOR(S) : Hiroshi Ito et al.

It is certified that error appears in the above-identified patent and that said Letters Patent is hereby corrected as shown below:

On the Title Page

Change:
"(72) Inventors: Hiroshi Ito, Narashino (JP); Takaya Nakagawa, Narashino (JP); Yoichi Kitsuta, Narashino (JP)"

To:
---(72) Inventors: Hiroshi Ito, Narashino-shi, Chiba (JP); Takaya Nakagawa, Narashino-shi, Chiba (JP); Yoichi Kitsuta, Narashino-shi, Chiba (JP)---

Signed and Sealed this
Nineteenth Day of November, 2019

Andrei Iancu
*Director of the United States Patent and Trademark Office*